(12) United States Patent
DeDonato

(10) Patent No.: US 8,954,211 B2
(45) Date of Patent: Feb. 10, 2015

(54) METHODS AND SYSTEMS FOR CONFIGURING SENSOR ACQUISITION BASED ON PRESSURE STEPS

(71) Applicant: Teledyne Instruments, Inc., Thousand Oaks, CA (US)

(72) Inventor: Mathew DeDonato, Worchester, MA (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 167 days.

(21) Appl. No.: 13/645,913

(22) Filed: Oct. 5, 2012

(65) Prior Publication Data

US 2013/0090789 A1    Apr. 11, 2013

Related U.S. Application Data

(60) Provisional application No. 61/545,036, filed on Oct. 7, 2011.

(51) Int. Cl.
G01N 1/16 (2006.01)
G01N 33/18 (2006.01)

(52) U.S. Cl.
CPC .............. *G01N 1/16* (2013.01); *G01N 33/1886* (2013.01)
USPC ............................... 701/21; 702/2; 73/170.33

(58) Field of Classification Search
None
See application file for complete search history.

(56) References Cited

U.S. PATENT DOCUMENTS

| 4,202,034 | A | | 5/1980 | Bowditch et al. |
|---|---|---|---|---|
| 5,283,767 | A | * | 2/1994 | McCoy ............................ 367/4 |
| 5,869,756 | A | * | 2/1999 | Doherty et al. ............ 73/170.29 |
| 6,916,219 | B2 | * | 7/2005 | Tokhtuev et al. ............... 441/29 |
| 7,040,157 | B2 | * | 5/2006 | Glasgow et al. ........... 73/170.29 |
| 8,272,262 | B2 | * | 9/2012 | Cabrera et al. ............. 73/170.29 |

OTHER PUBLICATIONS

Dolan et al., "Cooperative Aquatic Sensing Using the Telesupervised Adaptive Ocean Sensor Fleet," Proc. SPIE 7473, Remote Sensing of the Ocean, Sea Ice, and Large Water Regions 2009, 747307, Sep. 9, 2009 (12 pages).

Downing et al., "An Autonomous Expendable Conductivity, Temperature, Depth Profiler for Ocean Data Collection," U.S. Department of Energy, Oct. 1992 (8 pages).

Podnar et al., "Networked Architecture for Robotic Environmental Ocean Science Sensors," Robotics Institute, Carnegie Mellon University, Paper 176, Jan. 2008 (5 pages).

* cited by examiner

*Primary Examiner* — Michael J Zanelli
(74) *Attorney, Agent, or Firm* — K&L Gates LLP

(57) ABSTRACT

Technologies are provided for underwater measurements. A system includes an underwater vessels including: a plurality of sensors disposed thereon for measuring underwater properties; and a programmable controller configured to selectively activate the plurality of sensors based at least in part on underwater pressure. A user may program at what pressure ranges certain sensors are activated to measure selected properties, and may also program the ascent/descent rate of the underwater vessel, which is correlated with the underwater pressure.

16 Claims, 3 Drawing Sheets

METHODS AND SYSTEMS FOR CONFIGURING SENSOR ACQUISITION BASED ON PRESSURE STEPS

CROSS-REFERENCE TO RELATED PATENT APPLICATIONS

This application claims priority from Provisional Application U.S. Application 61/545,036, filed Oct. 7, 2011. This application is incorporated hereby by reference in its entirety as if fully set forth herein.

STATEMENT OF GOVERNMENT INTEREST

The present invention may have been made, at least in part, with support from NASA award number NNX09AP51G. The Government may have certain rights in this invention.

BACKGROUND

Underwater vehicles (such as floats) may be used to measure physical and chemical properties of the ocean, detect underwater objects, and image seafloors or lakebeds. Various sensors such as pressure sensors, chemical sensors, temperature sensors, and sonars may be disposed on an underwater vessel. The underwater vessel may be tethered/towed from a platform, such as a ship, anchored to the hull of the ship, or may be an unmanned underwater vehicle (UUV) or autonomous underwater vehicle (AUV).

SUMMARY

Systems, apparatuses, and methods are provided for underwater measurements. In some embodiments, a system is provided comprising an underwater vessel comprising a plurality of sensors disposed thereon for measuring underwater properties including pressure; and a programmable controller configured to select one or more of the plurality of sensors to activate and/or sample based at least in part on an underwater pressure.

In embodiments, a method is provided for measuring underwater properties, comprising: measuring, by a pressure sensor, a current pressure; comparing, by one or more computers, the current pressure to pressure threshold limits for a plurality of respective pressure ranges, wherein each of the respective pressure ranges is associated with a respective set of one or more of the sensors, and activating and/or sampling, by the one or more computers, a respective one of the sets of one or more of the sensors when the current pressure range is within the pressure range associated with the respective one set of sensors.

In embodiments, a method for measuring underwater properties is provided comprising: measuring, by a pressure sensor, a current pressure; comparing, by one or more computers, the current pressure to pressure threshold limits for a plurality of respective pressure ranges, wherein each of the respective pressure ranges is associated with a respective set of one or more of the sensors; comparing, by one or more computers, a current time and/or date to a plurality of sets of data and/or time ranges, wherein the respective sets of the one or more sensors are associated with respective time and/or date ranges, and activating and/or sampling, by one or more computers, a respective one of the sets of one or more of the sensors when the current pressure range is within the pressure range associated with the respective one set of sensors and a current time and/or date is within the time and/or date range associated with the respective one set of sensors.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

The foregoing and other aspects, embodiments, and features of the present teachings may be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

DETAILED DESCRIPTION

Following below are more detailed descriptions of various concepts related to, and embodiments of, inventive methods and apparatus for underwater measurements and controls. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

In various embodiments disclosed herein, measurements are made during "profiling" of water, where a float is ascending or descending through the water. The profile may be a vertical profile over a column of water, and/or have a significant or insignificant lateral span during the ascent or descent. In embodiments, a mechanism is implemented to control when different sensors are used/activated throughout a profile.

Figure 1:
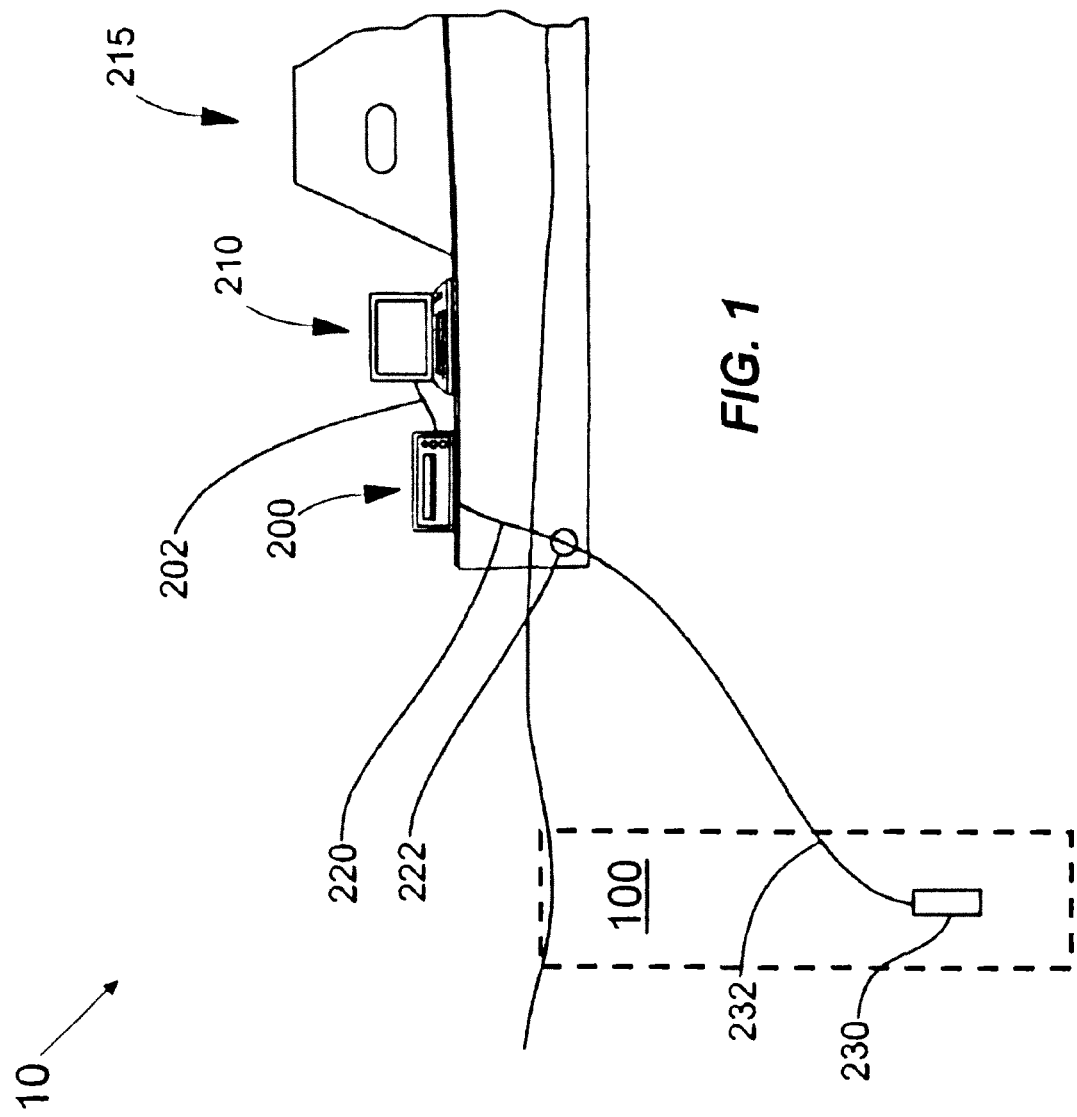
FIG. 1 is a schematic diagram of an example underwater measurement system according to one embodiment of the invention.

FIG. 1 is a schematic diagram illustrating a system 10 configured to measure underwater properties such as salinity, temperature, flow rate, etc. of a water volume. In embodiments, the water volume may comprise a vertical column 100. In embodiments, the water volume may comprise an angled column. In embodiments, the water volume may comprise a shape that varies based at least in part on a horizontal speed component. In embodiments, a float 230 may be used that has a plurality of sensors disposed therein. Note that the term "float" means a vessel that may ascend or descend through a volume of water or other liquid. Although embodiments are disclosed with water as the liquid, the invention is not limited to this liquid.

In embodiments, a top surface or remote modem 200 may communicate with the float 230. In embodiments, the float 230 may be powered and/or towed by a surface vessel 215 or an underwater vessel 215. In embodiments, the float 230 may be fully autonomous and without tethering cables. In embodiments, the modem 200 may connect to float 230 via a cable 220, via a port 222, and underwater cable 232, or wirelessly, to name a few. In embodiments, the float 230 may be managed by a computer 210, which may be connected to the modem 200 by various available means such as cable 202, or wirelessly. In embodiments, a computer for managing the float 230 may be disposed in the float 230, itself. The computer in the float 230 may then communicate with the computer on the vessel 215 via the modem 200.

During ascent or descent, a profile of parameters of the water volume 100 may be measured by sensors onboard the float 230, and transmitted to the modem 200 and computer 210 for analysis. In embodiments, some or all of the analysis may be performed by a computer on-board the float 230. In embodiments, a pressure sensor disposed on the float 230 may be coupled to a processing circuit or control circuit configured to process measurement of the pressure of the water in the area around the vessel. In embodiments, the processing circuit may then be configured to select one or more sensors for activation, sensing, or reading based at least in part on the sensed pressure. As noted, the processing circuit may be disposed in the float 230 and/or may be disposed in the vessel.

In embodiments, users require a variety of sensor packages on their underwater vessels such as floats, but do not need to use all of these sensors through an entire water volume. This leads to a scenario where data collected is then discarded. The energy used by the float 230 to collect and/or to sample the data is wasted. In embodiments, conserving energy may be important for autonomous underwater floats that are designed to function independently for many days.

In embodiments, a control circuit may be used to measure and/or sample the measurement of all or a selected set of sensors at predetermined pressure points or in predetermined pressure ranges. In embodiments, the control circuit may use "Pressure tables" to determine when to measure and/or sample. In embodiments, pressure tables may be programmed into the floats 230 by manufacturers. In embodiments, the pressure tables may not be changeable in the field. In embodiments, the pressure tables may be changeable in the field either remotely or by the operator.

In embodiments, the control circuit may comprise a comparison circuit for comparing current pressure from the pressure sensor to predetermined pressures in a pressure table. In embodiments, the control circuit may compare current pressure from the pressure sensor to upper and lower threshold limits that define one or more pressure ranges.

In embodiments, a profile may be stored in a memory in either the float 230 or the vessel 215, for example in the form of a table. In embodiments, the table may be divided into a plurality of pressure ranges defined by upper and lower thresholds. Within the given range, one or more of the sensors may be activated and/or sampled and/or used selectively or differently.

In embodiments, behavior of the float 230 may be controlled based at least in part on the particular pressure range. In embodiments, an ascent rate and/or a descent rate may be controlled based at least in part on the particular pressure range. In embodiments, the control circuit (as set by the user or as pre-set) may be pre-programmed to cause different sensors to sample and/or to activate at different points or ranges in the water volume 100. In embodiments, the control circuit (as set by the user or as pre-set) may be pre-programmed to cause different sensors to sample and/or activate at different points or ranges in the water volume 100 with different resolutions (number of samples in the pressure range) in the data profiles. In embodiments, the program may be stored in a non-transitory computer-readable medium onboard the float 230, implemented as an application-specific integrated circuit (ASIC), a field-programmable gated array (FPGA). In embodiments, the program may be stored in a non-transitory computer-readable medium, implemented in the remote computer 210, as an application-specific integrated circuit (ASIC), a field-programmable gated array (FPGA).

Profile threshold levels (which may be editable by the user) may be used to describe how the various sensors and float behaviors are activated and/or sampled while profiling, and are shown in the example Table 1 below. Each profile may be divided into a plurality of pressure ranges, within which sensors may be used differently.

For example, Table 1 divides the pressure into:
1000 dbar to 700 dbar (row 1)
700 dbar to 300 dbar (row 2)
300 dbar the surface (row 3)

TABLE 1

| | Pressure (dbar) | Interval (dbar) | Slow (Y/N) | Sensor 1 | Sensor 2 | Sensor 3 | Sensor 4 |
|---|---|---|---|---|---|---|---|
| 1 | 1000 | 10 | N | ON | OFF | OFF | ON |
| 2 | 700 | 25 | Y | OFF | ON | ON | ON |
| 3 | 300 | 5 | N | ON | ON | OFF | ON |

"Pressure" in the Table indicates the pressure at which to start the sampling scheme. The "interval" entries indicate when (within each pressure range) sensors are activated/used. For example, an interval entry of 25, in row 2, indicates use of sensors at pressures of 700, 675, 650, 625, 600, 575, . . . , 300 dbar. The data profile resolution would be lower in this case as compared with pressure range 1, where an interval of 10 dbar is adopted, or pressure range 3, where an interval of 5 dbar is adopted.

"Slow" in the Table indicates whether the float should ascend slowly (e.g., at 0.04 dbar/sec) or quickly (at 0.08 dbar/sec) during the particular pressure range. In embodiments, specific speeds of ascent or descent may be set. This may be modified to allow for other accent or descent rates as well. By programming the speed of ascent and/or descent parameter, the user may control the data sampling speed. Additional float behaviors may be added or substituted in place of the pressure parameter to control the ascent and/or descent of the float 230 through the water volume. For example, the ascent and/or the descent behavior may be based at least in part on salinity as measured by the salinity sensor, and/or the temperature, and/or the flow rate.

"Sensors 1-4" with indicators "ON" indicate at what pressure step the sensor is turned on. Pressure intervals may be as small or as large as needed, and pressure steps may be as close or as far apart as needed. In embodiments, for those pressure ranges (corresponding to depth ranges) in which the sensors are programmed to be "OFF," the specified sensors may be turned "OFF" or in dormant states to save energy. In embodiments, the user may program as many parameters as desired.

In embodiments, a commercially available float (e.g., Teledyne Webb Research Apex float) or a non-commercially available float may be implemented with the inventive embodiments disclosed herein and used for, for example, bio-geo-chemical profiling measurements. A variety of commercially-available sensors may be used, such as a Satlantic/WETLabs bio-optical sensor system, or sensors to be developed in the future may be used.

In embodiments, different sets of sensors, and/or different sampling modes, may be used between different pressure ranges (corresponding to different depths) and at different times, such as different times during the day. In addition, float behavior (such as ascent rate or descent rate) may be controlled, depending on the pressure range. In embodiments, sensors may be grouped into sets, with properties such as data verbosity (e.g., amount of data in a text stream) levels. For example, where data transmission bandwidth is limited, a sensor with a high verbosity level may be combined with sensors with low verbosity levels or which are set to have low verbosity levels based on sampling rate. In embodiments, sensors may be grouped into sets based at least in part on whether they are active-optic measurement sensors (e.g., radiating light or other radiation into the water and measuring a response), or radiometry-related measurement sensors (e.g., measuring a response in the water from sunlight). In embodiments, profiles may be divided into pressure ranges, with each sensor set being programmed separately within each pressure range. In embodiments, profiles may be updated remotely (e.g., via the Iridium satellite system), which may be important when ocean properties to be measured change due to season or float location. An onboard controller may receive the instructions from the user to program the control table such as the example illustrated as Table 1.

Figure 2:
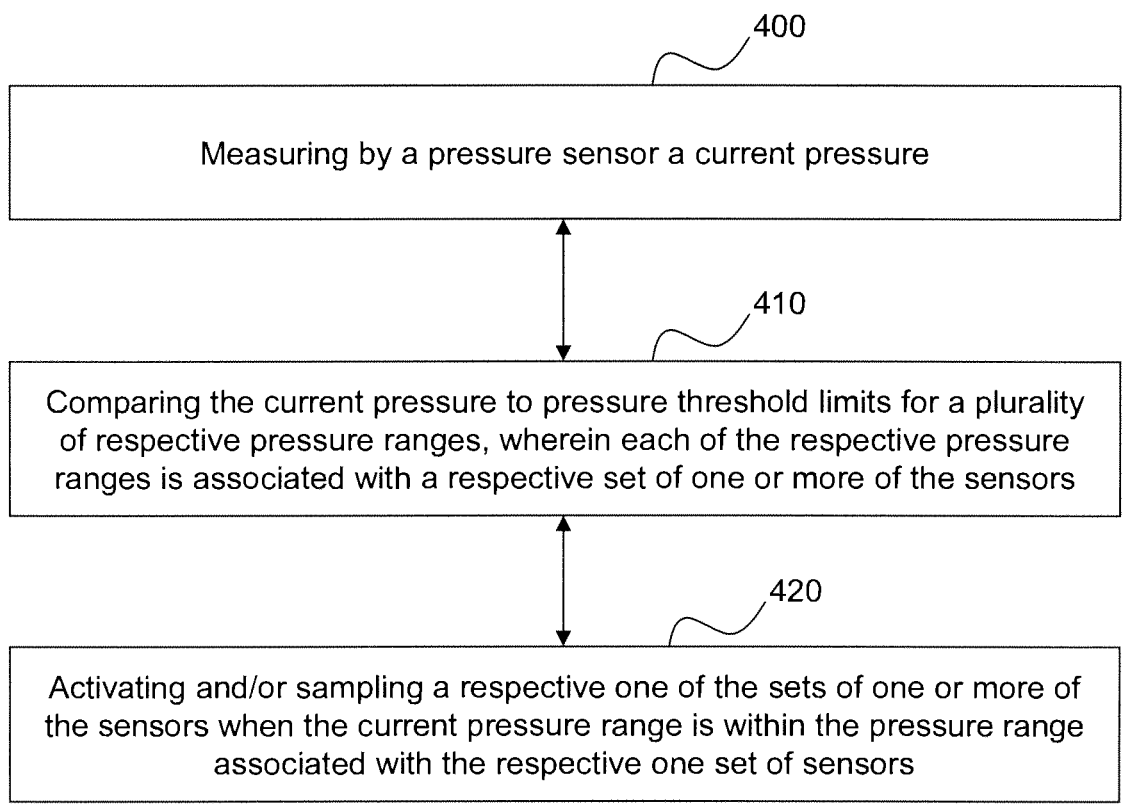
FIG. 2 is a flowchart representing an embodiment.

In embodiments as illustrated in FIG. 2, a method for measuring underwater properties may comprise a step 400 of measuring, by a pressure sensor, a current pressure. In embodiments, the method may further comprise the step 410 of comparing, by one or more computers, the current pressure to pressure threshold limits for a plurality of respective pressure ranges, wherein each of the respective pressure ranges is associated with a respective set of one or more of the sensors. In embodiments, the method may further comprise the step 420 of activating and/or sampling, by the one or more computers, a respective one of the sets of one or more of the sensors when the current pressure range is within the pressure range associated with the respective one set of sensors.

In embodiments, the method may further comprise controlling, by the one or more computers, an ascent or descent rate of the underwater vessel based at least in part on the current pressure.

In embodiments of the method, a respective frequency of activation and/or sampling is associated with each of the respective pressure ranges, and the activating and/or sampling step may activate and/or sample the set of one or more of the sensors with the associated frequency when the current pressure is within the pressure range associated with the respective one set.

In embodiments of the method, the frequency of activation and/or sampling is further associated with a time range and/or a date range, and the activating and/or sampling step may activate and/or sample the set of one or more of the sensors with the associated frequency only when a current time and or date is within is within the time and/or date range associated with the respective frequency.

In embodiments of the method, the programmable controller is configured to control an ascent or descent rate of the underwater vessel based at least in part on the underwater pressure.

Figure 3:
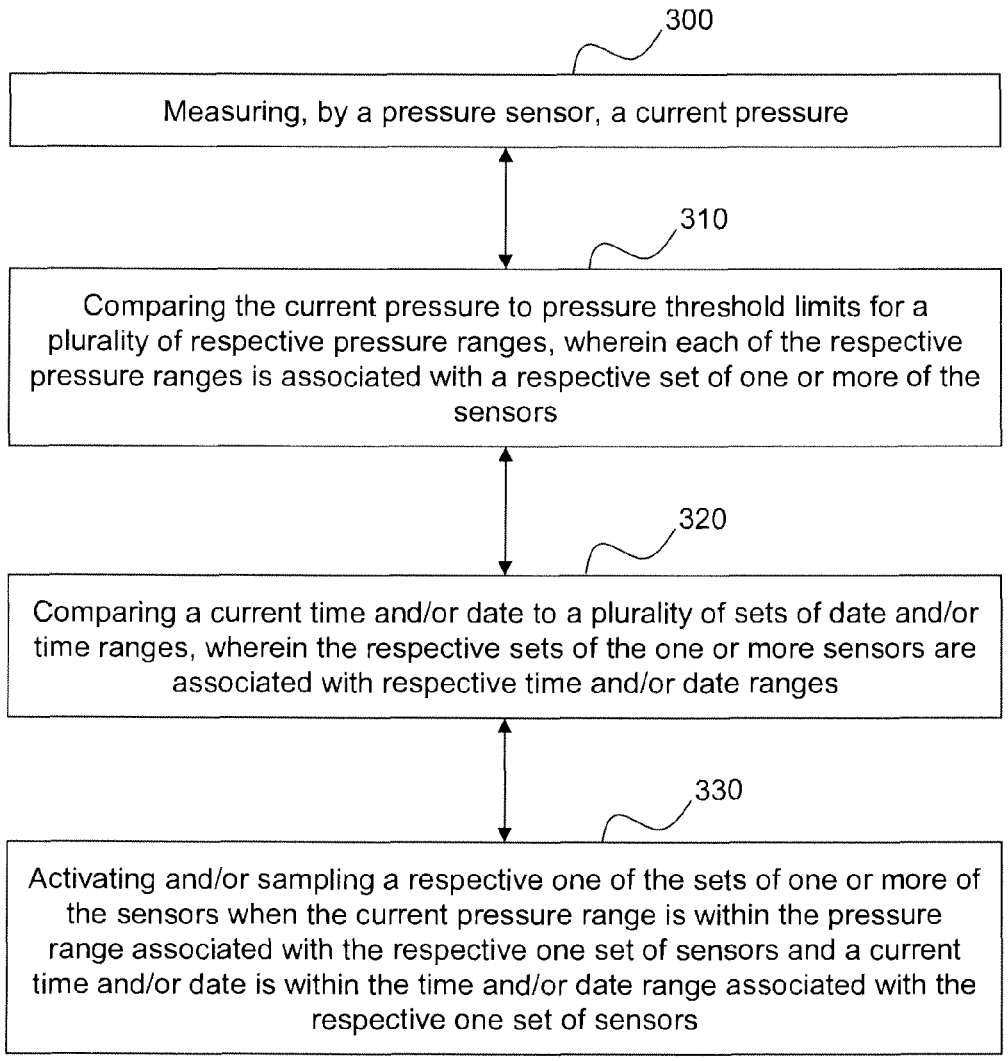
FIG. 3 is a flowchart representing another embodiment.

In embodiments as reflected in FIG. 3, a method for measuring underwater properties may comprise the step 300 of measuring, by a pressure sensor, a current pressure. In embodiments, the method may further comprise the step 310 of comparing, by one or more computers, the current pressure to pressure threshold limits for a plurality of respective pressure ranges, wherein each of the respective pressure ranges is associated with a respective set of one or more of the sensors. In embodiments, the method may further comprise the step 320 of comparing, by one or more computers, a current time and/or date to a plurality of sets of date and/or time ranges, wherein the respective sets of the one or more sensors are associated with respective time and/or date ranges. In embodiments, the method may further comprise the step 330 of activating and/or sampling a respective one of the sets of one or more of the sensors when the current pressure range is within the pressure range associated with the respective one set of sensors and a current time and/or date is within the time and/or date range associated with the respective one set of sensors.

In embodiments of the method, the sensors are grouped into the sets based at least in part on one or more selected from the group of data verbosity level and whether active-optic measurements are required and whether radiometry-related measurements are required.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention may be implemented in any of numerous ways. For example, some embodiments may be implemented using hardware, software or a combination thereof. When any aspect of an embodiment is implemented at least in part in software, the software code may be executed on any suitable processor or collection of processors, whether provided in a single device or computer or distributed among multiple devices/computers.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

The invention claimed is:

1. A system comprising:
an underwater vessel including:
a plurality of sensors disposed thereon for measuring underwater properties including pressure; and
a programmable controller configured to selectively activate one or more of the plurality of sensors based at least in part on an underwater pressure measurement from the pressure sensor, wherein at least one of the plurality of sensors is turned off or in a dormant state unless the least one of the plurality of sensors is activated.

2. The system as defined in claim 1, wherein the programmable controller is configured to control an ascent or descent rate of the underwater vessel based at least in part on the underwater pressure.

3. The system as defined in claim 1, wherein the programmable controller is configured:
to activate and/or sample a pressure sensor measuring to obtain a current pressure;
to compare the current pressure to pressure threshold limits for a plurality of respective pressure ranges, wherein each of the respective pressure ranges is associated with a respective set of one or more of the sensors, and
to activate and/or sample a respective one of the sets of one or more of the sensors when the current pressure range is within the pressure range associated with the respective one set of sensors.

4. A system comprising:
an underwater vessel including:
a plurality of sensors disposed thereon for measuring underwater properties including pressure; and
a programmable controller configured to select one or more of the plurality of sensors to activate and/or sample based at least in part on an underwater pressure; and
wherein the programmable controller is configured to control an ascent or descent rate of the underwater vessel based at least in part on temperature measured by one of the sensors.

5. A system comprising:
an underwater vessel including:
    a plurality of sensors disposed thereon for measuring underwater properties including pressure; and
    a programmable controller configured to select one or more of the plurality of sensors to activate and/or sample based at least in part on an underwater pressure; and
    wherein the programmable controller is configured:
        to activate and/or sample a pressure sensor measuring to obtain a current pressure;
        to compare the current pressure to pressure threshold limits for a plurality of respective pressure ranges, wherein each of the respective pressure ranges is associated with a respective set of one or more of the sensors; and
    wherein a respective frequency of activation and/or sampling is associated with each of the respective pressure ranges; and
    wherein the programmable controller is configured to activate and/or to sample the set of one or more of the sensors with the associated frequency when the current pressure is within the pressure range associated with the respective one set.

6. The system as defined in claim 5, wherein the frequency of activation and/or sampling is further associated with a time range and/or a date range, and
wherein the programmable controller is configured to activate and/or to sample the set of one or more of the sensors with the associated frequency only when a current time and/or date is within is within the time and/or date range associated with the respective frequency.

7. The system as defined in claim 5, wherein the programmable controller is configured to control an ascent or descent rate of the underwater vessel based at least in part on the underwater pressure.

8. A system comprising:
an underwater vessel including:
    a plurality of sensors disposed thereon for measuring underwater properties including pressure; and
    a programmable controller configured to select one or more of the plurality of sensors to activate and/or sample based at least in part on an underwater pressure;
wherein the programmable controller is configured:
    to activate and/or sample a pressure sensor measuring to obtain a current pressure;
    to compare the current pressure to pressure threshold limits for a plurality of respective pressure ranges, wherein each of the respective pressure ranges is associated with a respective set of one or more of the sensors;
    to compare a current time and/or date to a plurality of sets of date and/or time ranges, wherein the respective sets of the one or more sensors are associated with respective time and/or date ranges; and
    to activate and/or sample a respective one of the sets of one or more of the sensors when the current pressure range is within the pressure range associated with the respective one set of sensors and a current time and/or date is within the time and/or date range associated with the respective one set of sensors.

9. A system comprising:
an underwater vessel including:
    a plurality of sensors disposed thereon for measuring underwater properties including pressure; and
    a programmable controller configured to select one or more of the plurality of sensors to activate and/or sample based at least in part on an underwater pressure;
    wherein the sensors are grouped into sets based at least in part on one or more selected from the group of data verbosity level and whether active-optic measurements are required and whether radiometry-related measurements are required.

10. A method for measuring underwater properties, comprising:
    measuring, by a pressure sensor, a current pressure;
    comparing, by one or more computers, the current pressure to pressure threshold limits for a plurality of respective pressure ranges, wherein each of the respective pressure ranges is associated with a respective set of one or more of the sensors, and
    activating and/or sampling, by the one or more computers, a respective one of the sets of one or more of the sensors when the current pressure range is within the pressure range associated with the respective one set of sensors; and
    wherein the respective set of one or more of the sensors is turned off or in a dormant state unless the respective set of one or more of the sensors is activated.

11. The method as defined in claim 10, further comprising:
    controlling, by the one or more computers, an ascent or descent rate of the underwater vessel based at least in part on the current pressure.

12. A method for measuring underwater properties, comprising:
    measuring, by a pressure sensor, a current pressure;
    comparing, by one or more computers, the current pressure to pressure threshold limits for a plurality of respective pressure ranges, wherein each of the respective pressure ranges is associated with a respective set of one or more of the sensors; and
    activating and/or sampling, by the one or more computers, a respective one of the sets of one or more of the sensors when the current pressure range is within the pressure range associated with the respective one set of sensors; and
    wherein a respective frequency of activation and/or sampling is associated with each of the respective pressure ranges; and
    wherein the activating and/or sampling step activates and/or samples the set of one or more of the sensors with the associated frequency when the current pressure is within the pressure range associated with the respective one set.

13. The method as defined in claim 12,
    wherein the frequency of activation and/or sampling is further associated with a time range and/or a date range, and
    wherein the activating and/or sampling step activates and/or samples the set of one or more of the sensors with the associated frequency only when a current time and/or date is within the time and/or date range associated with the respective frequency.

14. The method as defined in claim 12, wherein the programmable controller is configured to control an ascent or descent rate of the underwater vessel based at least in part on the underwater pressure.

15. A method for measuring underwater properties, comprising:
    measuring, by a pressure sensor, a current pressure;
    comparing, by one or more computers, the current pressure to pressure threshold limits for a plurality of respective pressure ranges, wherein each of the respective pressure ranges is associated with a respective set of one or more of the sensors; and activating and/or sampling, by the one or more computers, a respective one of the sets of one or more of the sensors when the current pressure range is within the pressure range associated with the respective one set of sensors; and wherein the sensors are grouped into the sets based at least in part on one or more selected from the group of data verbosity level and whether active-optic measurements are required and whether radiometry-related measurements are required.

16. A method for measuring underwater properties, comprising:

measuring, by a pressure sensor, a current pressure;

comparing, by one or more computers, the current pressure to pressure threshold limits for a plurality of respective pressure ranges, wherein each of the respective pressure ranges is associated with a respective set of one or more of the sensors;

comparing, by one or more computers, a current time and/or date to a plurality of sets of date and/or time ranges, wherein the respective sets of the one or more sensors are associated with respective time and/or date ranges, and activating and/or sampling, by one or more computers, a respective one of the sets of one or more of the sensors when the current pressure range is within the pressure range associated with the respective one set of sensors and a current time and/or date is within the time and/or date range associated with the respective one set of sensors.

* * * * *